United States Patent [19]

Detty

[11] Patent Number: 4,916,127

[45] Date of Patent: Apr. 10, 1990

[54] MIXED CHALCOGENIDE PYRYLIUM SALTS OF A LEWIS BASE

[75] Inventor: Michael R. Detty, Rochester, N.Y.

[73] Assignee: Eastman Kodak Company, Rochester, N.Y.

[21] Appl. No.: 261,289

[22] Filed: Oct. 24, 1988

[51] Int. Cl.$^4$ .................. C07D 421/06; A61K 31/33
[52] U.S. Cl. .................................. 514/183; 514/432; 514/451; 540/1; 544/13; 544/415
[58] Field of Search ................ 540/1; 544/13, 415; 514/183, 432, 451

[56] References Cited

U.S. PATENT DOCUMENTS 4,365,017 12/1982 Detty .................................. 430/83
4,584,258 4/1986 Detty et al. ......................... 430/270

OTHER PUBLICATIONS

Cotton and Wilkinson, Advanced Inorganic Chemistry, p. 572 (1962).
Gordon et al., The Chemists Companion, pp. 383–386, (1972).

*Primary Examiner*—Robert Gerstl
*Attorney, Agent, or Firm*—Dana M. Schmidt

[57] ABSTRACT

There are disclosed certain pyrylium salts and a method of making them. The dyes are useful both medicinally in photodynamic therapy and in photoconductive compositions, photoresist and lithographic compositions or optical recording discs. The salts are mixed seleno- or telluropyrylium compounds having a singlet oxygen quantum efficiency of at least 0.005 when exposed as described at wavelengths between about 650 and 1000 nanometers, and a Lewis base anion.

3 Claims, No Drawings

MIXED CHALCOGENIDE PYRYLIUM SALTS OF A LEWIS BASE

FIELD OF THE INVENTION

This invention relates to novel pyrylium dyes, and a method of making such dyes.

BACKGROUND OF THE INVENTION

Chalcogenopyryliums in the past have been made using either of the two following schemes:

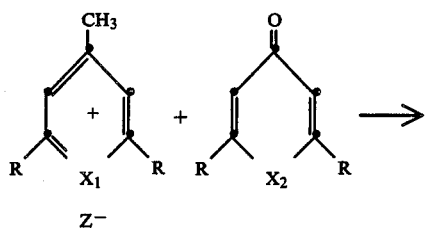
(i)

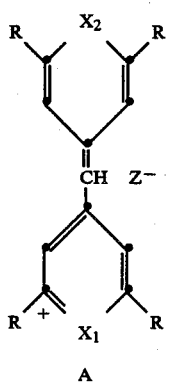
A or

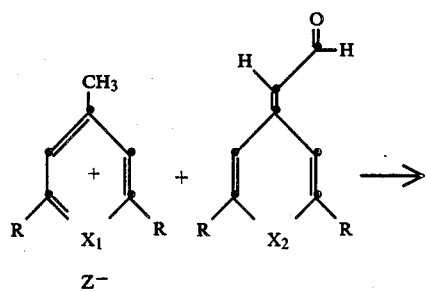
(ii)

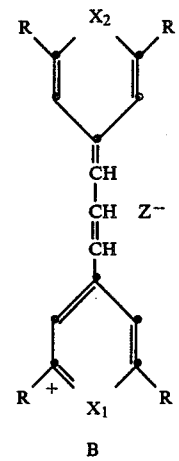
B wherein R is a variety of substituents and $X_1$ and $X_2$ are a chalcogen and are the same or different, and Z is an anion. These reactions have been successful in general in producing relatively pure results. However, I have discovered that a special case exists if $X_1$ and $X_2$ are mixed, that is if $X_1$ is Se or Te and $X_2$ is some other chalcogenide, and if Z is a Lewis base. In such a case the end product is unstable, and decomposes back to a scrambled mixture of the starting materials. Thus, at best only a fifty percent pure desired product can be achieved. For pharmaceutical compositions, such a result is unacceptable. This is particularly unfortunate when $Z^-$ is a halide for maximum water-solubility, since halides are reasonable Lewis bases. Impurities will, of course, ruin the effectiveness of the final product, such as when used in cancer therapy.

It is true that compounds of the structure A and B noted above have been taught where $X_1=Se$ and $X_2=Te$. However, in those cases Z was not a Lewis base so that the purity of the product A or B was not jeopardized. Examples of such teachings can be found in U.S. Pat. No. 4,584,258, wherein $Z^-$ is $BF_4^-$ or $ClO_4^-$.

Thus, prior to this invention there has been a substantial need to find a method for synthesizing relatively pure pyrylium dyes having mixed Se and Te atoms, and a Lewis base anion.

SUMMARY OF THE INVENTION

I have discovered that these seleno- and telluropyryliums can be made using an ion exchange.

More specifically, in accord with one aspect of this invention, there is provided a pharmaceutically pure form of a seleno- or telluropyrylium dye having the following structural formula:

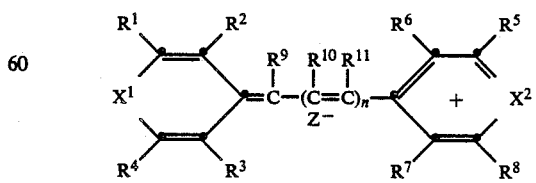

wherein $R^1$, $R^4$, $R^5$, and $R^8$ are selected from hydrogen, aryl, heteroaryl, or alkyl from one to twelve carbon atoms; $R^2$, $R^3$, $R^6$, and $R^7$ are selected from hydrogen, alkyl, aryl, or alkyl or aryl derivatives such as alkylthio, arylthio, alkylseleno, arylseleno, alkyltelluro or aryltelluro of from one to twelve carbon atoms; halogen; hydroxy; alkoxy; amino; $R^9$, $R^{10}$, and $R^{11}$ are selected from hydrogen, alkyl and alkoxy of from one to twelve carbon atoms, halogen and cyano; n is 0, 1, or 2; $X^1$ and $X^2$ are chalcogenides different from each other except that one is either Se or Te, and $Z^-$ is a water-soluble Lewis base.

In accord with another aspect of the invention, there is provided a method of making such dyes, comprising the steps of (a) selecting a compound having the following structural formula:

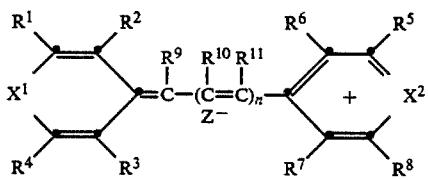

wherein $R^1$, $R^2$, $R^3$, $R^4$ etc through $R^8$, n, $X^1$ and $X^2$ are as defined above, but $Z^-$ is an anion other than a Lewis base; and (b) mixing the compound with an ion exchange resin containing a Lewis base, for a time sufficient to exchange the non-Lewis base anion with the Lewis base anion.

Thus, it is an advantageous feature of the invention that pharmaceutically pure mixed Se and Te pyrylium dyes are provided with Lewis bases.

It is a related advantageous feature of the invention that such dyes are provided with anions that render them more readily water soluble.

Other advantageous features will become apparent upon reference to the following Description of the Preferred Embodiments.

DESCRIPTION OF THE PREFERRED EMBODIMENTS

I have discovered novel pyrylium dyes particularly effective in photodynamic therapy (pdt) of cancer cells, most particularly for differentiated carcinomas and melanoma cells, and a method of making them. They are also useful in photoconductive, photoresist, lithographic or optical recording compositions.

The invention features pharmaceutically pure pyrylium dyes containing mixed chalcogenides in which one is either Te or Se. Preferred are dyes having the following structural formula:

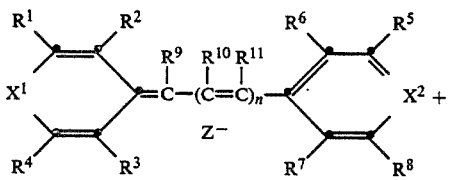

wherein $R^1$, $R^4$, $R^5$, and $R^8$ are selected from hydrogen, aryl of six to twelve carbon atoms, for example, phenyl, naphthyl and the like; heteroaryl of six to twelve carbon atoms, for example, pyridyl, thienyl, furyl, etc., or alkyl of from one to twelve carbon atoms, for example methyl, ethyl, propyl, iso-propyl, butyl, t-butyl, hexyl, heptyl, octyl, dodecyl and the like; $R^2$, $R^3$, $R^6$, and $R^7$ are selected from hydrogen, amino; hydroxy; halo such as chloro, fluoro, iodo, and bromo; or alkyl, aryl or alkyl or aryl derivatives such as alkylthio, arylthio, alkoxy, alkylseleno, arylseleno, alkyltelluro or aryltelluro, all from one to twelve carbon atoms, for example, methyl, ethyl, propyl, hexyl, dodecyl, phenyl, naphthyl, methylthio, hexylthio, dodecylthio, phenylthio, the corresponding seleno equivalents of these, and the corresponding telluro equivalents of these, methoxy, propoxy, and the like; $R^9$, $R^{10}$, and $R^{11}$ are selected from hydrogen, halo such as chloro, fluoro, bromo and iodo; cyano; and alkyl and alkoxy of from one to twelve carbon atoms, for example methyl, ethyl, propyl, iso-propyl, butyl, t-butyl, hexyl, heptyl, octyl, dodecyl, methoxy, ethoxy, propoxy, butoxy, t-butoxy, heptoxy, dodecyloxy and the like; n is 0, 1 or 2; $X^1$ and $X^2$ are as defined above, and Z is a water-soluble Lewis base. As used herein, "pharmaceutically pure" means purity levels accepted by the FDA, namely with impurities not exceeding 2% of the dye weight, so that for the dye synthesized, at least 98% is the dye of the identified structure. A dye that is impure may still have pdt efficacy, but such would require FDA approval on each component separately as well as on the combination, an undesirable expense for a result that is most likely to be less satisfactory than results obtained using the pharmaceutically pure dye.

Also as used herein, "alkyl" includes substituted alkyl, such as by hydroxy groups.

Useful Lewis base anions include halides such as chloride, bromide and the like; and $CH_3SO_3^-$.

Thus, useful pyryliums of this invention include a salt formed by any of the aforesaid useful anions, with the pyryliums listed in Table I.

The most preferred examples of useful pyryliums include the following:

TABLE I

| Dye No. | Name |
| --- | --- |
| 1. | 2,6-Di-t-butyl-4-[3-(2,6-di-t-butyl-4H-telluropyran-4-ylidene)-1-propen-1-yl]selenopyrylium chloride |
| 2. | 2,6-Di-t-butyl-4-[3-(2,6-di-t-butyl-4H-telluropyran-4-ylidene)-1-propen-1-yl]thiopyrylium chloride |
| 3. | 2,6-Di-t-butyl-4-[3-(2,6-di-t-butyl-4H-telluropyran-4-ylidene)-1-propen-1-yl]pyrylium chloride |
| 4. | 2,6-Di-t-butyl-4-[3-(2,6-di-t-butyl-4H-selenopyran-4-ylidene)-3-methyl-1-propen-1-yl]telluropyrylium chloride |
| 5. | 2,6-Di-t-butyl-4-[3-(2,6-di-t-butyl-4H-selenopyran-4-ylidene)-1-propen-1-yl]thiopyrylium bromide |
| 6. | 2,6-Di-t-butyl-4-[3-(2,6-di-t-butyl-4H-selenopyran-4-ylidene)-1-propen-1-yl]pyrylium chloride |
| 7. | 2,6-Di-t-butyl-4-(2,6-di-t-butyl-4H-thiopyran-4-ylidenemethyl)-3-iodo-telluropyrylium chloride |
| 8. | 2,6-Di-(4-hydroxy-n-butyl)-4-(2,6-di-t-butyl-4H-selenopyran-4-ylidenemethyl)telluropyrylium chloride |

SYNTHESIS

Since Z is to be a Lewis base, for example halide or mesylate and $X^1$ and $X^2$ are to be different, then in order to obtain a relatively pure yield, it is necessary to use the following procedure: The desired dye with an anion that is *not* a Lewis base anion, is admixed with an ion exchange resin containing a Lewis base, and an ion exchange is allowed to occur. In addition, this procedure can be used to prepare a Lewis base salt of even those dyes in which $X^1$ and $X^2$ are identical.

PREPARATION EXAMPLES

The starting material, that is, the dyes with an anion that is *not* a Lewis base, were prepared by either of the two following general reactions:

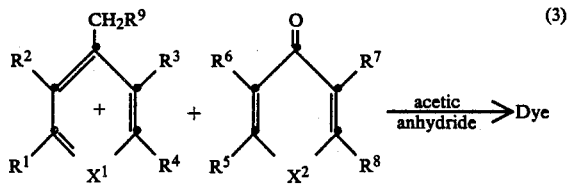
(3)

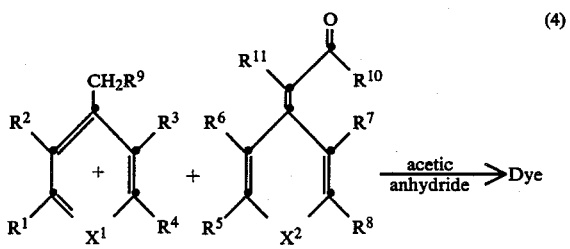
(4)

wherein $R^1$–$R^{11}$, $X^1$, $X^2$, n, and Z are chosen as described above except that Z is not a Lewis base, for example, tetrafluoroborate, hexafluorophosphate, or perchlorate.

Preparation 1.—of the Chloride Salt of Dye 1

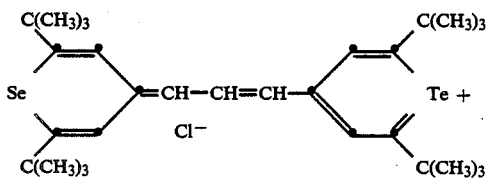

The perchlorate salt of Dye 1 (0.19 g; 0.27 mmol) and 1.5 g of Amberlite IRA-400 (Cl) ion exchange resin were stirred in 75 mL of methanol for 4 hours. The ion exchange resin was removed by filtration and the filter cake was washed with 10 mL of methanol. The combined filtrates were stirred for an additional 2 hours with 1.5 g of the ion exchange resin. The ion exchange resin was removed by filtration and the filter cake was washed with 10 mL of methanol. The combined filtrates were concentrated in vacuo. The residue was dissolved in 5 mL of acetonitrile which was then diluted with ether to 50 mL. Chilling precipitated the dye as yellow-green crystals which were collected by filtration, washed with ether, and dried to give 0.14 g (82%) of the dye, mp 213.5°–215° C. $\lambda_{max}$ (CH$_2$Cl$_2$) 786 nm ($\epsilon$ 304,000). $^1$H NMR (CD$_3$OD) δ8.87 (t, 1H, J=13.3 Hz), 7.78 (br s, 4H), 6.76 (d, 1H, J=13.3 Hz), 6.71 (d, 1H, J=13.3 Hz), 1.47 (s, 27H), 1.45 (s, 9H). Anal. Calcd for C$_{29}$H$_{43}$SeTe.Cl: C, 55.0; H, 6.8; Cl, 5.6. Found: C, 55.2; H, 6.8; Cl, 5.5. The 82% yield is completely consistent with "pharmaceutically pure", in that the 18% loss is simply due to material losses in the method. The dye obtained did in fact meet the "pharmaceutically pure" criterion noted above.)

Preparation 2.—of the Chloride Salt of Dye 2

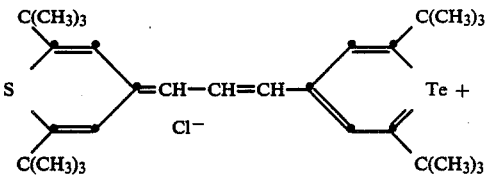

The hexafluorophosphate salt of Dye 2 (0.070 g, 0.10 mmol) was dissolved in 20 mL of methanol. One gram of the Amberlite IRA-400 (Cl) ion exchange resin was added. The resulting mixture was stirred at ambient temperature for four hours. The ion exchange resin was removed by filtration and the filter cake was washed with 10 mL of methanol. The combined filtrates were concentrated. The residue was recrystallized from 1 mL of acetonitrile and 20 mL of ether. Chilling precipitated copper bronze needles of the dye which were collected by filtration, washed with ether, and dried to give 0.048 g (81%) of Dye 2. mp 200.5°–203.5° C. $\lambda_{max}$ (water) 745 nm ($\epsilon$ 110,000). $^1$H NMR (CD$_3$OD) δ 8.77 (t, 1H, J=13 Hz), 7.93 (br s, 2H), 7.7 (br s, 2H), 6.69 (d, 2H, J=13 Hz), 1.48 (s, 18H), 1.42 (s, 18H). Anal. Calcd for C$_{29}$H$_{43}$STeCl: C, 59.4; H, 7.4; Cl, 6.0. Found: C. 59.3; H, 7.4; Cl, 5.8.

Comparative Preparation Example

Attempted Preparation of the Chloride Salt of Dye 1 with Condensation Technology 2,6-Di-tert-butyl-4-methylselenopyrylium chloride (6.00 g, 18.8 mmol) and (2,6-di-tert-butyl-telluropyran-4-ylidene)acetaldehyde (6.72 g, 19.4 mmol) in 20 mL of acetic anhydride were heated on a steam bath for eleven minutes. The reaction mixture was cooled to ambient temperature and 15 mL of acetonitrile was added. The resulting solution was filtered through a pad of glass wool. The filtrate was diluted with 250 mL of ether and the resulting solution was chilled. The dye precipitated as copper-bronze crystals which were collected by filtration, washed with ether, and dried to give 10.51 g (88%) of the dye. $^1$H NMR and absorption spectroscopies showed the product to be a one to two to one mixture of Dye 2a to Dye 2 to Dye 2b, where dye 2a and 2b are the analogs having Se or Te respectively in both of the two heteroatom rings of the dye. This mixture is expected from a statistical distribution of the heteroatoms if random scrambling of the heteroatoms were to occur during reaction.

Utility Example

The following discussion of medicinal utility is taken from a related application co-filed by Detty and Powers, Ser. No. 261,288, entitled "Photodynamic Therapy Using Seleno- or Telluropyrylium Salts".

In the photodynamic therapy (pdt) method of treating differentiated carcinomas or melanoma in mammals, the dye is particularly useful when added to a pharmaceutically acceptable carrier. The pharmaceutically acceptable carrier can be selected from a variety of carriers, such as a solvent that will sufficiently dissolved the pyrylium dye. Among preferred examples of a suitable carrier solvent is a minimal amount (100 mg of dye/ml of 95% ethanol) diluted with phosphate buffered saline to produce a dye salt concentration of 1 mM. Still other useful example include a 5% dextrose solution in water, or a mixture of ethanol and a polyol such as polyethoxylated caster oil, avaliable from the National Cancer Institute as "Diluent No. 12."

Still other acceptable carrier solvents include, dimethyl sulfoxide (DMSO) for intravesical treatment, and isotonic saline for IV and IP injections.

Still other carriers that are useful include the following:

Materials such as gelatin, natural sugars such as sucrose or lactose, lecithin, pectin, starch (for example cornstarch), alginic acid, tylose, talc, lycopodium, silica (for example collodial silica), glucose cellulose, cellulose derivatives, for example cellulose ethers in which the cellulose hydroxyl groups are partially etherified with lower aliphatic alcohols and/or lower saturated oxyalcohols (for example, methyl hydroxypropyl cellulose, methyl cellulose, hydroxyethyl cellulose), stearates, e.g., methyl stearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono-, di-, and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono-, or polyvalent alcohols and polyols such as glycerine, mannitol, sorbitol, pentaerythritol, ethyl alcohol, diethylene glycol, triethylene glycol, ethylene glycol, propylene glycol, dipropylene glycol, poly(ethylene glycol), and other poly(alkylene glycols), as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, ethylene distearate, ethylene dilaurate, ethylene diacetate, monoacetin, triacetin, glyceryl oleate, esters of polyvalent alcohols that are etherified, benzyl benzoate, dioxolane, glycerin formal, tetrahydrofurfuryl alcohol, polyglycol ethers of 1 to 12 carbon atoms alcohols, lactamide, lactates, e.g., ethyl lactate, ethyl carbonate, silicones (especially medium viscosity dimethyl polysiloxane), magnesium carbonate and the like.

Still other additives, and methods of preparation of the compositions, can be found in the extant literature.

Useful methods of delivery of the dye and carrier include intravenous (IV), intraperitoneal (IP) intravesical, and arterial injection.

The dosage levels depend uypon which pyrylium dye is being used on which cancer. Such dosage may be determined by one skilled in the art, using the techniques described in Goodman and Gilman's "The Pharmacological Basis of Therapeutics" (6th edition), pages 1675-1737, subtitled "Design and Optimization of Dosage Regimens" (Macmillan Publishing Co., New York, 1980). Based on dosages commonly experienced for pdt agents, and the correlation that has been shown between clinical tests and the $LD_{50}$ dosages found in animal protocols, it is estimated the dosages for human consumption would be: 1.0 to 7.5 mg/kg of body weight, using various injection protocols that do not exceed this level, followed by phototherapy within an appropriate time.

The ability of the dyes of this invention to function as a cancer-treating agent is in part a reflection of the ability of the dye to generate singlet oxygen in air-saturated solution. (As used herein, "air-saturated solution" means a solution of dye exposed to the atmosphere.) In studying a variety of chalcogenopyrylium dyes, only those dyes containing a selenium or tellurium atom show any appreciable generation of singlet oxygen upon irradiation. Fortuitously, selenopyrylium and telluropyrylium dyes have absorption maxima that are shifted to the red relative to their pyrylium and thiopyrylium analogues. Table II contains examples of chalcogenopyrylium dyes, their quantum efficiencies for singlet oxygen generation, and their absorption maxima. (In this Table, Me=Methyl, and t-BU=tertiary butyl.)

TABLE II
Quantum Efficiencies of Singlet Oxygen Generation ($\Phi$) and Absorption Maxima ($\lambda_{max}$) for Chalcogenopyrylium Dyes

| Dye | $X^1$ | $X^2$ | $R^1$ | $R^2$ | $R^3$ | $R^4$ | n | Z | $\Phi(^1O_2)$ | $\lambda_{max}$ (solvent) |
|---|---|---|---|---|---|---|---|---|---|---|
| 1 | Te | Se | t-Bu | H | H | H | 1 | Cl | 0.09 | 786 nm ($CH_2Cl_2$) |
| 2 | Te | S | t-bu | H | H | H | 1 | Cl | 0.07 | 745 nm ($H_2O$) |
| 3 | Te | O | t-Bu | H | H | H | 1 | Cl | 0.06 | 700 nm ($H_2O$) |
| 4 | Se | Te | t-Bu | Me | H | H | 1 | Cl | 0.01 | 803 nm ($CH_2Cl_2$) |
| 5 | Se | S | t-bu | H | H | H | 1 | Br | 0.008 | 700 nm ($H_2O$) |
| 6 | Se | O | t-Bu | H | H | H | 1 | Cl | 0.005 | 660 nm ($H_2O$) |

*Estimated

All of these have a $\Phi$ value that is at least 0.005. Also, $\lambda_{max}$ of Table II is in each case 650 nm or higher, and in most cases above 700 nm.

The amount of light exposure needed for the pdt is generally on the order of at least about 15 Joules/$cm^2$, if the wavelengths used are 700 nm or above, that is, the wavelengths effective to penetrate most body tissues. Increased amounts are useful if the dye has a value of $\Phi$ of only 0.005 or slightly larger. The wavelength of exposure should be picked to match $\lambda_{max}$. Preferred methods of exposure include lasers such as conventional argon-pumped dye lasers using, for example, laser dye LDS 751, or laser diodes with a fixed wavelength of >700 nm, e.g., 800±2 nm, coupled by a 400 μm quartz fiber optic. Also useful are tungsten lights with cut-off filters that block light below 730 nm.

The following examples illustrate the effectiveness of this invention in treating the noted cancers.

EXAMPLES 1-8

In Vitro Testing of Glioma, Melanoma and Squamous Cell Carcinoma

Several selenopyrylium dyes and telluropyrylium dyes from Table I that generated singlet oxygen upon irradiation in air-saturated methanol were examined in vitro in mammalian cell cultures for their effectiveness as agents for photodynamic therapy. These results are compiled in Table III. The cell lines that were examined include U251 (mouse glioma), B-16 melanoma (mouse melanoma), and FADU (duman squamous cell carcinoma). As controls, HSK1 (normal human skin fibroblasts) and CV-1 (normal monkey kidney cells) were used.

In vitro cell cultures were grown in antibiotic-free growth medium DMEM-F12 supplemented to 10% with fetal bovine serum and adjusted to 4.5 mM with L-glutamine. DMEM-F12 is a 1:1 mixture of Dulbecco's modified Eagle's medium (Gibco) and Ham's nutrient mixture F12 (Gibco). Prior to cell seeding, multiwell plates were blackened with spray paint, coating the external walls of each well to minimize light scattering from well to well. Subconfluent cell cultures were trypsinized and plated at a concentration of $10^5$ cells per 2 $cm^2$ well. Cells were allowed to incubate overnight at 37° C. in a humidified atmosphere before dye and/or light exposure.

Stock solutions of the chalcogenopyrylium dyes were prepared at 1 mM concentration by sonication in 95% ethanol in the dark. These stock solutions were diluted with growth medium to the desired concentration. Dyes were protected from light throughout the entire experimental procedure until the time for irradiation. The length of time between dye injection and light exposure was from about 0.35 to about 0.5 hour. Standard treatment time for dye exposure was 1 hour. The dye containing medium was replaced with fresh growth medium prior to irradiation. Eighteen to twenty-four hours later, the remaining metabolically active cells were evaluated by the MTT colorimetric assay and/or cell counting. Assays were performed in triplicate with standard deviations generally of less than 10%. Percent kill was determined from mean optical density of the treated samples and that of the control (untreated) samples for the MTT analysis and from mean cell counts for these two groups for the cell-counting method. (See Table III).

Near-infrared and visible light from three sources were employed in these assays. Tungsten light (100-200 mW) was used to assess low milliwatt multiple wavelength effects. An argon-pumped dye laser (Model 150 Aurora, Cooper Lasersonics, Inc., Santa Clara, Calif.) with laser dye LDS 751 (Exciton Chemical Co., Inc., Dayton, Ohio) and a peak wavelength of 785±5 nm was coupled by a 1 μm quartz fiberoptic to a microlens assembly that gave a uniform mode of distribution of light intensity. Thirdly, a laser diode (Model 2430-H2, Spectra Diode Laboratories, Inc., San Jose, Calif.) with a fixed wavelength of 800±2 nm provided light energy in the near infrared. The diode was coupled by a 400 μm quartz fiberoptic with a clear and polished end. For laser irradiation experiments, the distance of the fiber tip from the well bottom was adjusted so that the laser irradiation exactly covered the 2 $cm^2$ target area. A distal power meter (Model 2000, Coherent, Inc., Auburn, Calif.) was used to determine the energy output of the laser source.

TABLE III

In Vitro Testing of Selenopyrylium and Telluropyrylium Dyes as Photosensitizers for Photodynamic Therapy in Mammalian Cells

| Ex. No. | Dye | Z | Concentration, M | Cell Line[a] | Total Energy J $cm^{-2}$ | % Surviving Fraction Dark | % Surviving Fraction Light | Light Source[b] |
|---|---|---|---|---|---|---|---|---|
| Control 1 | 1 | Cl | $5 \times 10^{-8}$ | HSK1 | 15 | 99.0 | 97.0 | C |
| Control 2 | 1 | Cl | $5 \times 10^{-8}$ | CV1 | 15 | 100.0 | 99.0 | A |
| 1 | 1 | Cl | $5 \times 10^{-8}$ | U251 | 15 | 85.0 | 65.0 | C |
| 2 | 1 | Cl | $5 \times 10^{-8}$ | B-16 | 15 | 99.0 | 0.03 | A |
| 3 | 1 | Cl | $5 \times 10^{-8}$ | FADU | 15 | 99.0 | 0.1 | A |
| Control 3 | 3 | Cl | $1 \times 10^{-7}$ | HSK1 | 15 | 99.0 | 99.0 | A |
| Control 4 | 3 | Cl | $1 \times 10^{-7}$ | CV1 | 15 | 100.0 | 99.0 | A |
| 4 | 3 | Cl | $1 \times 10^{-7}$ | U251 | 15 | 90.0 | 58.0 | A |
| 5 | 3 | Cl | $1 \times 10^{-7}$ | B-16 | 15 | 99.0 | 0.1 | A |
| 6 | 3 | Cl | $1 \times 10^{-7}$ | FADU | 15 | 99.0 | 0.05 | A |
| Control 5 | 6 | Cl | $1 \times 10^{-6}$ | CV1 | 15 | 100.0 | 99.0 | A |
| 7 | 6 | Cl | $1 \times 10^{-6}$ | B-16 | 15 | 99.0 | 0.2 | A |
| 8 | 6 | Cl | $1 \times 10^{-6}$ | FADU | 15 | 99.0 | 0.2 | A |

[a]HSK1, normal human skin fibroblasts; CV1, normal monkey kidney cells; U251, mouse glioma; B-16, mouse melanoma; FADU, human squamous cell.
[b]A, tungsten light source with a cutoff filter at approxamately 730 nm; B, dye laser with emission maximum at 785 ± 5 nm; C, diode laser with emission at 800 ± 2 nm.

It can be seen from Table III that most of the cancer cells in question were effectively killed by the dyes of the invention, but only after exposure to the light energy. (At least a 5% reduction in survival after light exposure is needed, beyond the survival level in the dark, to establish a phototherapeutic effect.)

The invention has been described in detail with particular reference to preferred embodiments thereof, but it will be understood that variations and modifications can be effected within the spirit and scope of the invention.

What is claimed is:

1. A pharmaceutically pure form of a seleno- or telluropyrylium dye having the following structural formula:

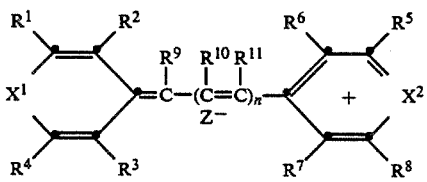

wherein $R^1$, $R^4$, $R^5$, and $R^8$ are selected from hydrogen, aryl, heteroaryl, or alkyl from one to twelve carbon atoms; $R^2$, $R^3$, $R^6$, and $R^7$ are selected from hydrogen, alkyl, aryl, alkylthio, arylthio, alkylseleno, arylseleno, alkyltelluro or aryltelluro of from one to twelve carbon atoms; halogen; hydroxy; alkoxy; and amino; $R^9$, $R^{10}$, and $R^{11}$ are selected from hydrogen, alkyl and alkoxy of from one to twelve carbon atoms, halogen and cyano; n is 0, 1 or 2; $X^1$ and $X^2$ are chalcogenides different from each other except that one is either Se or Te, and $Z^-$ is a Lewis base selected from the group consisting of chloride, bromide and $CH_3SO_3^-$, said pure form having impurities not exceeding 2% of the dye by weight.

2. A dye as defined in claim 1, selected from the group consisting of 2,6-Di-t-butyl-4-[3-(2,6-di-t-butyl-4H-telluropyran-4-ylidene)-1-propen-1-yl]selenopyrylium chloride;

2,6-Di-t-butyl-4-[3-(2,6-di-t-butyl-4H-telluropyran-4-ylidene)-1-propen-1-yl]thiopyrylium chloride;

2,6-Di-t-butyl-4-[3-(2,6-di-t-butyl-4H-telluropyran-4-ylidene)-1-propen-1-yl]pyrylium chloride;

2,6-Di-t-butyl-4-[3-(2,6-di-t-butyl-4H-selenopyran-4-ylidene)-3-methyl-1-propen-1-yl]telluropyrylium chloride;

2,6-Di-t-butyl-4-[3-(2,6-di-t-butyl-4H-selenopyran-4-ylidene)-1-propen-1-yl]thiopyrylium bromide;

2,6-Di-t-butyl-4-[3-(2,6-di-t-butyl-4H-selenopyran-4-ylidene)-1-propen-1-yl]pyrylium chloride;

2,6-Di-t-butyl-4-(2,6-di-t-butyl-4H-thiopyran-4-ylidenemethyl)-3-iodo-telluropyrylium chloride; and 2,6-Di-(4-hydroxy-n-butyl)-4-(2,6-di-t-butyl-4H-selenopyran-4-ylidenemethyl)telluropyrylium chloride.

3. A pure form of a dye as defined in claim 1, and further including a pharmaceutically acceptable carrier comprising an ethanol solution diluted with phosphate-buffered saline.

* * * * *